(12) United States Patent
Parsonage

(10) Patent No.: US 8,449,903 B2
(45) Date of Patent: May 28, 2013

(54) CROSSLINKED BIOABSORBABLE MEDICAL DEVICES

(75) Inventor: Edward Parsonage, St. Paul, MN (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 324 days.

(21) Appl. No.: 12/794,270

(22) Filed: Jun. 4, 2010

(65) Prior Publication Data

US 2010/0310624 A1 Dec. 9, 2010

Related U.S. Application Data

(60) Provisional application No. 61/185,015, filed on Jun. 8, 2009.

(51) Int. Cl.
*A61F 2/00* (2006.01)

(52) U.S. Cl.
USPC .......................................................... 424/423

(58) Field of Classification Search
None
See application file for complete search history.

(56) References Cited

U.S. PATENT DOCUMENTS

| | | |
|---|---|---|
| 4,475,972 A | 10/1984 | Wong |
| 4,882,390 A | 11/1989 | Kolb |
| 4,900,792 A | 2/1990 | Chen et al. |
| 4,950,258 A | 8/1990 | Kawai et al. |
| 4,997,904 A | 3/1991 | Domb |
| 5,163,952 A | 11/1992 | Froix |
| 5,670,161 A | 9/1997 | Healy et al. |
| 5,762,625 A | 6/1998 | Igaki |
| 5,800,519 A | 9/1998 | Sandock |
| 5,994,667 A | 11/1999 | Merdan et al. |
| 6,024,764 A | 2/2000 | Schroeppel |
| 6,169,084 B1 | 1/2001 | Langer et al. |
| 6,245,103 B1 | 6/2001 | Stinson |
| 6,500,204 B1 | 12/2002 | Igaki |
| 6,563,080 B2 | 5/2003 | Shapovalov et al. |
| 6,599,314 B2 | 7/2003 | Mathis |
| 6,696,666 B2 | 2/2004 | Merdan et al. |

(Continued)

FOREIGN PATENT DOCUMENTS

| WO | 95/26762 A1 | 10/1995 |
|---|---|---|
| WO | 2004032799 A2 | 4/2004 |

OTHER PUBLICATIONS

Heller, Jorge, Handbook of Biodegradable Polymers, Abraham J. Domb, Joseph Kost, David M. Wiseman, Eds., CRC Press, 1997, Chapter 6.

(Continued)

*Primary Examiner* — Carlos Azpuru
*Assistant Examiner* — Casey Hagopian
(74) *Attorney, Agent, or Firm* — Mayer & Williams PC; David B. Bonham

(57) ABSTRACT

The present invention is directed to bioabsorbable medical devices which are introduced into the body of a subject in a first configuration and deformed in the subject's body to a second configuration. The devices generally include at least one bioabsorbable expandable device component that comprises at least one type of biodegradable polymer. In accordance with an aspect of the invention, the expandable device component is crosslinked while in an expanded configuration. The crosslinked device component is then heated to a temperature above the glass transition temperature (Tg) of the material forming the device component. Upon heating to this temperature, the device component is compressed into a contracted configuration and cooled to below the Tg of the material to maintain the contracted configuration.

15 Claims, 1 Drawing Sheet

U.S. PATENT DOCUMENTS

| | | |
|---|---|---|
| 6,696,667 B1 | 2/2004 | Flanagan |
| 6,867,389 B2 | 3/2005 | Shapovalov et al. |
| 7,351,421 B2 | 4/2008 | Sung et al. |
| 2003/0083732 A1 | 5/2003 | Stinson |
| 2003/0236514 A1 | 12/2003 | Schwarz |
| 2004/0181271 A1 | 9/2004 | DeSimone et al. |
| 2007/0142903 A1* | 6/2007 | Dave .................... 623/1.22 |
| 2008/0001330 A1 | 1/2008 | Huang et al. |
| 2008/0036119 A1* | 2/2008 | Kanazawa .................... 264/494 |
| 2008/0097576 A1 | 4/2008 | Cottone et al. |
| 2008/0208321 A1* | 8/2008 | Venkatraman et al. ...... 623/1.19 |

OTHER PUBLICATIONS

Heller, et al., Scaffolding in Tissue Engineering, Peter X. Ma and Jennifer Elisseeff, Eds., CRC Press, 2005, Chapter 7.

Engelberg et al., "Physico-mechanical properties of degradable polymers used in medical applications: a comparative study" Biomaterials, 12 (1991) 292-304.

Yoshii et al., "Modification of biodegradable polymers by radiation crosslinking technique with polyfunctional monomers" IRaP 2002, 5th International Symposium on Ionizing Radiation and Polymers, Sep. 21-26, 2002, Hôtel Le Chantecler, Sainte-Adèle, Canada, P-060, in Nuclear Instruments and Methods in Physics Research B 208 (2003) 370-373.

Yamashiro et al., "Recyclable Shape-memory and Mechanical Strength of Poly(lactic acid) Compounds Cross-linked by Thermoreversible Diels-Alder Reaction" Polymer Journal, 40(7), 2008, 657-662.

Quynh et al., "Properties of crosslinked polylactides (PLLA & PDLA) by radiation and its biodegradability" European Polymer Journal, 43(5), May 2007, 1779-1785.

Chmielewski, "Worldwide developments in the field of radiation processing of materials in the down of 21st century", Nukleonika 2006; 51(Supplement 1): S3-S9.

* cited by examiner ic device components, the bioabsorbable medical devices in accordance with the invention may further comprise additional components, for example, non-bioabsorbable components and/or additional bioabsorbable components.

CROSSLINKED BIOABSORBABLE MEDICAL DEVICES

RELATED APPLICATIONS

This application claims priority from U.S. provisional application 61/185,015, filed Jun. 8, 2009, which is incorporated by reference herein in its entirety.

BACKGROUND OF THE INVENTION

Bioabsorbable medical devices are widely used in the practice of modern medicine. For example, bioabsorbable stents are of continuing interest because they have the potential to provide the mechanical functions required of stents, while at the same time eliminating various long-term effects associated with biostable stents.

Current bioabsorbable polymeric devices, including bioabsorbable polymeric stents, generally suffer from recoil upon expansion. Without wishing to be bound by theory, it is believed that the recoil has both acute and chronic elements that are associated with the plastic deformation and subsequent residual stresses arising upon deployment from a collapsed to an expanded state in the body.

SUMMARY OF THE INVENTION

The present invention is directed to bioabsorbable medical devices which are introduced into the body of a subject in a first configuration and deformed in the subject's body to a second configuration. The devices generally include at least one bioabsorbable expandable device component that comprises at least one type of biodegradable polymer.

In accordance with one aspect of the invention, the expandable device component is crosslinked while in an expanded configuration. The crosslinked device component is then heated to a temperature above a glass transition temperature (Tg) of the material forming the device component. Upon heating to this temperature, the device component is compressed into a contracted configuration and cooled to below the Tg of the material to maintain the contracted configuration.

An advantage of the present invention is that bioabsorbable expandable device components may be provided which have reduced recoil upon expansion.

Another advantage of the present invention is that bioabsorbable expandable device components may be provided which have improved radial strength upon expansion.

Yet another advantage of the present invention is that, for a stent, the preceding advantages may be obtained while maintaining securement of the stent on the balloon catheter during storage and implantation.

These and other aspects, embodiments and advantages of the present invention will become immediately apparent to those of ordinary skill in the art upon review of the Detailed Description and Claims to follow.

DETAILED DESCRIPTION OF THE INVENTION

Figure 1:
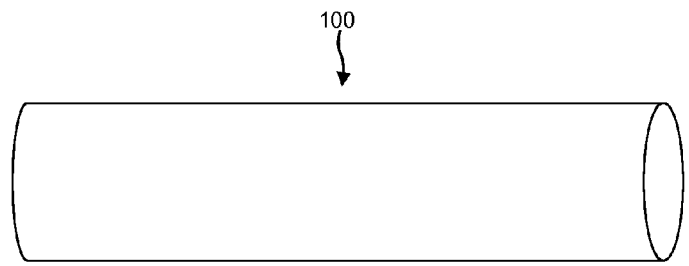
FIG. 1 is a schematic perspective view of a bioabsorbable polymeric tube prior to being laser cut into a stent, in accordance with an embodiment of the invention.

As noted above, the present invention is directed to bioabsorbable medical devices which are introduced into the body of a subject in a first configuration and deformed in the subject's body to a second configuration. The devices generally include at least one bioabsorbable expandable device component that comprises at least one type of biodegradable polymer.

In accordance with an aspect of the invention, the expandable device component is formed and crosslinked in an expanded configuration. The crosslinked device component is then heated to a temperature above the glass transition temperature (Tg) of the material forming the device component. Upon heating to this temperature, the device component is compressed into a contracted configuration and cooled to below the Tg of the material to maintain the contracted configuration.

Without wishing to be bound by theory, it is believed that, due to the fact that the device component (e.g., a stent body, etc.) was previously crosslinked in an expanded state, the material has a shape memory of the device component in the expanded state, even when in a contracted state. In this way, a compensating force is provided in opposition to the recoil that is associated with device expansion from a contracted state (e.g., balloon deployment of a stent from a crimped state, etc.).

Materials for forming the device components of the invention include polymeric materials that display at least one high Tg. As used herein, a "high" Tg is a Tg that is approximately equal to or above body temperature (37° C.), more typically ranging from 40° C. to 50° C. to 75° C. to 100° C. or above. Multiple Tg's may be observed in some instances (e.g., where a material comprises a blend of two or more polymers that exhibit differing Tg's, where a material comprises a block copolymer having two or more polymer blocks that exhibit differing Tg's, etc.). Where a material has multiple Tg's, the material is preferably heated above at least one of the Tg's and in some embodiments above all of the Tg's. Tg values can be measured by differential scanning calorimetry (DSC), dynamic mechanical analysis (DMA) or thermomechanical analysis (TMA).

Particularly preferred are expandable devices which are constructed such that they can be inserted into a body lumen (e.g., blood vessels, etc.) while in a contracted configuration and expanded in vivo in the body lumen to an expanded configuration. Examples of such expandable devices include stents (including vascular stents such as coronary vascular stents and peripheral vascular stents including cerebral stents, urethral stents, ureteral stents, biliary stents, tracheal stents, gastrointestinal stents and esophageal stents), stent coverings, stent grafts, vascular grafts, septal defect devices, patent foramen ovale (PFO) devices, abdominal aortic aneurysm (AAA) devices (e.g., AAA stents, AAA grafts, etc.), embolization devices including cerebral aneurysm filler coils, and drug depots that are adapted for placement in an artery for treatment of the portion of the artery distal to the device.

As indicated above, bioabsorbable medical devices in accordance with the invention (e.g., stents, etc.) comprise one or more bioabsorbable expandable device components (e.g., a stent body, etc.) that comprise one or more biodegradable polymers. In addition to one or more bioabsorbable expandable device components, the devices of the invention may further optionally comprise one or more additional bioabsorbable components in some embodiments. For example, the devices may comprise one or more bioabsorbable layers that comprise one or more biodegradable polymers and one or more therapeutic agents, among many other possibilities. In other embodiments, the bioabsorbable expandable device component(s) constitute the entirety of the device.

Device components in accordance with the present invention are bioabsorbed by a subject upon implantation or insertion of the component into the subject.

"Bioabsorption" or "bioresorption" of a polymer-containing medical device component is defined herein to be a result of polymer biodegradation (as well as other in vivo disintegration processes such as dissolution, etc.) and is characterized by a substantial loss in vivo over time (e.g., the period that the component is designed to reside in a patient) of the original polymer mass of the device or component. For example, losses may range from 50% to 75% to 90% to 95% to 97% to 99% or more of the original polymer mass of the device component. Bioabsorption times may vary widely, with typical bioabsorption times ranging from days to months to years, depending on the application.

As used herein, a polymer is "biodegradable" if it undergoes bond cleavage along the polymer backbone in vivo, regardless of the mechanism of bond cleavage (e.g., enzymatic breakdown, hydrolysis, oxidation, etc.).

As used herein, "polymers" are molecules containing multiple copies (e.g., 5 to 10 to 25 to 50 to 100 to 250 to 500 to 1000 or more copies) of one or more constitutional units, commonly referred to as monomers. As used herein, "monomers" may refer to free monomers and to those are incorporated into polymers, with the distinction being clear from the context in which the term is used. As used herein, "homopolymers" are polymers that contain multiple copies of a single constitutional unit. "Copolymers" are polymers that contain multiple copies of at least two dissimilar constitutional units, examples of which include random, statistical, gradient, periodic (e.g., alternating) and block copolymers.

"Polymeric materials" are materials that comprise one or more types of polymers.

Although bioabsorbable stents are exemplified in the following paragraphs, it is clear from the above that the invention is applicable to other medical devices beyond stents.

In a particular embodiment of the invention, a bioabsorbable stent body comprising one or more types of polymers is crosslinked at a first diameter, which may be, for example, the intended deployment diameter of the stent body or a diameter that is somewhat greater (e.g., up to 100% greater) than the intended deployment diameter of the stent body. For a coronary stent, such first diameters may range, for example, from 2 to 5 mm. The stent body is then heated above the Tg of the stent body material at which point the stent body is compressed to a second diameter, which may be, for example, a diameter suitable for placement on a delivery device that is configured to expand the stent body in vivo (e.g., a balloon catheter) or a or a diameter that is somewhat less (e.g., up to 50% less), depending on the degree of rebound, if any. For a coronary stent, such second diameters may range, for example, from 1 to 1.5 mm. Typically, the second diameter ranges from 20% to 50% of the first diameter.

Stent bodies in accordance with the invention include stent bodies cut from tubular structures (e.g., laser cut stent bodies, mechanically cut stent bodies, etc.) and stent bodies formed from one or more filamentous elements.

Stent bodies may be formed in various ways. For example, referring to FIG. 1, in a first step, a bioabsorbable polymeric tube 100 may be formed which has a first diameter. For example, the polymeric tube may be formed with a diameter that is greater than or equal to the anticipated stent body diameter after deployment in the body of a subject. As another example, a tube may be formed at lesser diameter, but which may be axially extended and/or radially expanded in the solid state, thereby giving the polymer molecules a preferential orientation.

The tube is then cut to form a stent body having suitable structural elements. For example, a stent body 110 like that shown in FIG. 2, which comprises a plurality of expandable rings 110r (e.g., rings formed from wavy, sinusoidal, zig-zag, etc. structural elements) that are interconnected by longitudinal interconnection elements 110i, may be formed, among numerous other possibilities. Suitable laser cutting processes may be selected, for example, from those described in U.S. Pat. No. 6,867,389 to Shapovalov et al., U.S. Pat. No. 6,696,667 to Flanagan, U.S. Pat. No. 6,696,666 to Merdan et al., U.S. Pat. No. 6,563,080 to Shapovalov et al. or U.S. Pat. No. 5,994,667 to Merdan et al., among others.

Alternative processes to tube formation and cutting include, for example, melt molding techniques such as injection molding in which a polymer melt is introduced into a mold that reflects the shape of the stent body. The melt is then allowed to cool, whereupon the molded stent body is removed.

Numerous other stent designs may be improved using the materials and techniques of the present invention, including various filament-based stent designs. In this regard, stent body designs based on one or more filaments, which may configured in a wide variety of woven and non-woven stent body designs. For example, filament-based stent bodies may be formed using techniques such as coiling techniques and woven techniques (e.g., braiding or knitting techniques), among others. Examples of filament-based braided stent body designs include those having physical configurations analogous to the WALLSTENT® Stent System, Ultraflex™ Precision Colonic Stent System and WallFlex™ stent from Boston Scientific Corporation, Expander™ from Medicorp and a stent described in U.S. Pat. No. 5,800,519 to Sandock. Examples of filament-based knitted stent body designs include those having physical configurations analogous to the Strecker™ vascular stent from Boston Scientific Corporation, the Wiktor™ from Medtronic, and the ZA™ Stent from Cook. In another example, a filamentous stent body is formed as described in U.S. Pat. No. 4,475,972 to Wong, in which filaments are wound on a mandrel and overlying filament portions are simultaneously bonded with underlying filament portions.

It will be thus be clear to those of ordinary skill in the art that a wide range of expandable stent body designs may be improved using the materials and techniques of the present invention.

Regardless of the expandable stent body design employed, the stent body is crosslinked at a first expanded diameter using a suitable crosslinking process, examples of which are described in detail below.

After crosslinking, the stent body is then heated to above the Tg of the material forming the stent body. While heated above the Tg of the material, the stent body is reduced to a second contracted diameter and cooled. The stent body may be cooled, for example, by passively allowing the stent body to cool, by actively cooling the body by subjecting it to a stream of cooled fluid, and so forth.

Figure 2:
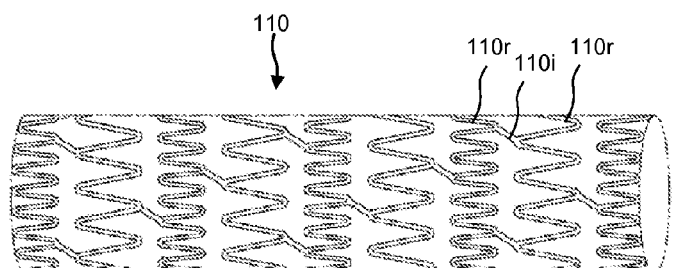
FIG. 2 is a schematic perspective view of the bioabsorbable polymeric tube of FIG. 1, after being laser cut into a stent, in accordance with an embodiment of the invention.
Figure 3:
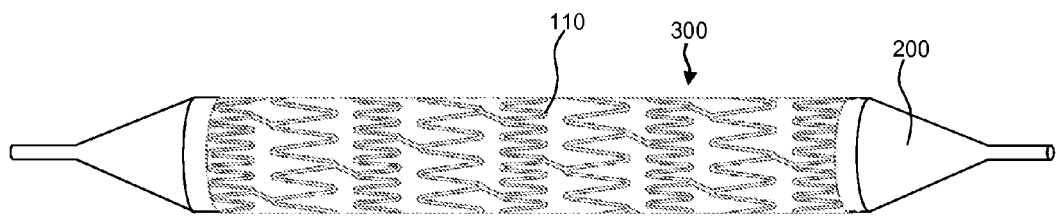
FIG. 3 is a schematic perspective view of the laser cut stent of FIG. 2, after being crimped onto a balloon, in accordance with an embodiment of the invention.

In a specific example, a stent 110 like that of FIG. 2 is crimped onto a balloon 200 at an elevated temperature (above the Tg of the material forming the stent body) and cooled, forming an assembly 300 such as that shown in FIG. 3. Such an assembly may be inserted into the body of a subject as is known in the art, at which point the balloon is inflated, expanding the stent into contact with the surrounding body lumen (e.g., a blood vessel wall).

Figure 4A:
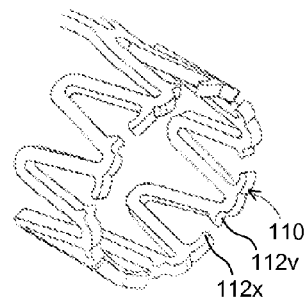
FIGS. 4A and 4B are schematic perspective views illustrating how a stent in accordance with an embodiment of the invention can be crimped and locked in a small-diameter profile.
Figure 4B:
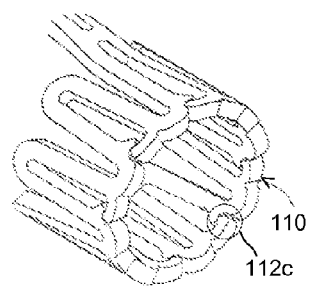

In certain embodiments, stent bodies in accordance with the invention may comprise a locking mechanism, for example, to more tightly retain the stent on a delivery device such as a balloon catheter after crimping. One example of such a stent is shown in partial perspective view in FIGS. 4A and 4B. The structural elements 110 of the stent shown contain convex regions 112x and concave regions 112v. When the stent 110 is crimped into a radially contracted state, the convex and concave regions engage one another to form coupled regions 112c as shown in FIG. 4B. The design shown has an appearance like that of a stent shown in Pub. No. US 2008/0097576 to Cottone et al. However, the stent shown is formed using the materials and processes described in accordance with the present invention. Other designs similar to those of Cottone et al. are described in U.S. Pat. No. 6,599,314 to Mathis and may be employed in the practice of the invention.

Examples of biodegradable polymers for forming medical device components in accordance with the invention (e.g., stent bodies, coating layers, etc.) may be selected from suitable members of the following, among many others: (a) polyester homopolymers and copolymers such as polyglycolide (PGA) (also referred to as polyglycolic acid), polylactide (PLA) (also referred to as polylactic acid) including poly-L-lactide, poly-D-lactide and poly-D,L-lactide, poly(beta-hydroxybutyrate), polygluconate including poly-D-gluconate, poly-L-gluconate, poly-D,L-gluconate, poly(epsilon-caprolactone), poly(delta-valerolactone), poly(p-dioxanone), poly(lactide-co-glycolide) (PLGA), poly(lactide-co-delta-valerolactone), poly(lactide-co-epsilon-caprolactone), poly(lactide-co-beta-malic acid), poly(beta-hydroxybutyrate-co-beta-hydroxyvalerate), poly[1,3-bis(p-carboxyphenoxy)propane-co-sebacic acid], and poly(sebacic acid-co-fumaric acid), among others, (b) polycarbonate homopolymers and copolymers such as poly(trimethylene carbonate), poly(lactide-co-trimethylene carbonate) and poly(glycolide-co-trimethylene carbonate), among others, (c) poly(ortho ester) homopolymers and copolymers such as those synthesized by copolymerization of various diketene acetals and diols, among others, (d) polyanhydride homopolymers and copolymers such as poly(adipic anhydride), poly(suberic anhydride), poly(sebacic anhydride), poly(dodecanedioic anhydride), poly(maleic anhydride), poly[1,3-bis(p-carboxyphenoxy)methane anhydride], and poly[alpha,omega-bis(p-carboxyphenoxy)alkane anhydrides] such as poly[1,3-bis(p-carboxyphenoxy)propane anhydride] and poly[1,3-bis(p-carboxyphenoxy)hexane anhydride], among others, (e) polyphosphazenes such as aminated and alkoxy substituted polyphosphazenes, and (f) amino-acid-based polymers including tyrosine-based polymers such as tyrosine-based polyarylates (e.g., copolymers of a diphenol and a diacid linked by ester bonds, with diphenols selected, for instance, from ethyl, butyl, hexyl, octyl and bezyl esters of desaminotyrosyl-tyrosine and diacids selected, for instance, from succinic, glutaric, adipic, suberic and sebacic acid), tyrosine-based polycarbonates (e.g., copolymers formed by the condensation polymerization of phosgene and a diphenol selected, for instance, from ethyl, butyl, hexyl, octyl and bezyl esters of desaminotyrosyl-tyrosine), tyrosine-based iminocarbonates, and tyrosine-, leucine- and lysine-based polyester-amides; specific examples of tyrosine-based polymers further include polymers that are comprised of a combination of desaminotyrosyl tyrosine hexyl ester, desaminotyrosyl tyrosine, and various di-acids, for example, succinic acid and adipic acid, among others.

Biodegradable homopolymers and copolymers for use in the invention include those that have high Tg's. Specific examples of high Tg biodegradable polymers include high Tg polyesters such as poly(l-lactide) (Tg 60-65° C.), poly(d,l-lactide) (Tg 55-60° C.), and poly(d,l-lactide-co-glycolide) (Tg 45-55° C.). Of these, poly(l-lactide) is semi-crystalline, which may provide additional strength to the polymeric region into which it is incorporated.

Examples of biodegradable polymers having high Tg's further include anhydride polymers that comprise one or more multivalent acids such as the following: sebacic acid (SA), bis-(p-carboxyphenoxylpropate) (CPP), isophthalic acid (ISO), hexadecandioic acid (HDA), fumaric acid (FA), terephthalic acid (TA), adipic acid (AA) and dodecanedioic acid (DD). Specific examples of high Tg polyanydrides include poly(CPP-ISO) (20:80) (Tg 110° C.), poly(CPP-ISO) (50:50) (Tg 100° C.), poly(CPP-ISO) (75:25) (Tg 230° C.), poly(CPP-ISO-SA) (15:58:27) (Tg 46° C.), poly(CPP-ISO-SA) (17:66:16) (Tg 83° C.), poly(CPP-ISO-TA) (50:40:10) (Tg 111.6° C.), and poly(CPP-ISO-TA) (25:60:15) (Tg 105° C.), among others. See U.S. Pat. No. 4,997,904 to Domb.

Biodegradable polymers having high Tg's further include poly(ortho esters). Examples of polyorthoesters include those that are formed by the reaction between a diketene acetal, for example, 3,9-diethylidene-2,4,8,10-tetraoxaspiro[5,5]undecane (DETOSU), with a diol. The use of rigid diols gives high Tg polymers. For example, the use of trans-cyclohexanedimethanol (tCDM) as a diol produces a poly(DETOSU-tCDM) copolymer having a Tg 120° C. Mixtures of rigid and flexible diols give intermediate Tg's. For example, copolymers of DETOSU, and a mixture of t-CDM and 1,6 hexane diol (1,6-HD, a flexible diol) have reported Tg's of 55° C. (t-CDM:1,6-HD=35:65), 84° C. (t-CDM:1,6-HD=70:30), and 95° C. (t-CDM:1,6-HD=90:10). Poly(ortho esters) formed from higher diols are more hydrophobic than those formed from lower diols and, consequently, have slower degradation rates. Because the ortho ester linkages are acid labile, degradation can be increased by introducing acidic species and decreased by the introduction of alkaline species. Examples of basic species that have been employed for this purpose include $Mg(OH)_2$. Examples of acidic species that have been employed include free acids and latent acids that are incorporated into the polymer structure. For further information on polyorthoesters see, e.g., *Handbook of Biodegradable Polymers*, Abraham J. Domb, Joseph Kost, David M. Wiseman, Eds., CRC Press, 1997, Chapter 6, *Scaffolding in Tissue Engineering*, Peter X. Ma and Jennifer Elisseeff, Eds., CRC Press, 2005, Chapter 7, and the references cited therein.

Specific examples of biodegradable polymers having high Tg's further include tyrosine-based polymers, including tyrosine-based iminocarbonates. A specific example of a polyiminocarbonate is poly(desaminotyrosine-tyrosoine-hexyl ester-iminocarbonate) (Tg 55° C.). For more information, see, e.g., I. Engelberg et al., *Biomaterials*, 12(1991)292-304 and the references cited therein.

Each biodegradable polymer has a characteristic degradation rate in the body. For example, PGA is a relatively fast-degrading material (weeks to months), whereas PLA is a relatively slow-degrading material (months to years).

As a general rule, mechanical properties improve with increasing molecular weight. For instance, the strength and modulus of PLA generally increases with increasing molecular weight. Degradation time generally increases with increasing initial molecular weight (i.e., a stent made of a low molecular weight polymer will, as a general rule, be bioabsorbed before a stent made of a high molecular weight polymer), which may be a desirable effect, depending on the application.

As previously indicated, the crystallinity of the polymeric material will also affect the mechanical properties as well as the degradation rate, with an increase in crystallinity typically resulting in an increase in strength and degradation time. For example, materials consisting of polyglycolide or of poly-L-lactide are known to have some degree of crystallinity, while those formed of DL-lactide, are reportedly amorphous. The desired degree of crystallinity may be adjusted in some embodiments by blending amorphous polymers with crystalline polymers.

Although stent bodies constructed of biodegradable polymers typically have a larger profile when placed on a delivery catheter (and thus when placed in a body lumen) than certain metal stents (to compensate for the typically lower strength of polymers relative to metals), stent bodies constructed of biodegradable polymers can provide various advantages relative to metal stents, including natural decomposition into non-toxic chemical species over a period of time. For example, PLA and PGA are degraded in vivo through hydrolytic chain scission to lactic acid and glycolic acid, respectively, which can then be converted to $CO_2$ and then eliminated from the body by respiration, if necessary.

Biodegradable polymers such as those listed above, among others, along with any optional agents, such as crosslinking agents, therapeutic agents, and so forth, may be formed into polymeric device components, including stent bodies and precursors to stent bodies (e.g., tubes, filaments, etc.), using a variety of techniques.

For example, where the biodegradable polymers have thermoplastic characteristics, a variety of thermoplastic processing techniques may be used to form polymeric components from the same. Using these techniques, a polymeric component can be formed, for instance, by (a) first providing a melt that contains polymer(s) and any other optional agents such crosslinking agents, therapeutic agents, and so forth, and (b) subsequently cooling the melt. Examples of thermoplastic processing techniques include compression molding, injection molding, blow molding, spraying, vacuum forming and calendaring, extrusion into sheets, fibers, rods, tubes and other cross-sectional profiles of various lengths, and combinations of these processes. Using these and other thermoplastic processing techniques, a wide variety of polymeric components can be formed.

Other processing techniques besides thermoplastic processing techniques may also be used to form the polymeric components of the present invention, including solvent-based techniques. Using these techniques, polymeric components can be formed, for instance, by (a) first providing a solution or dispersion that contains polymer(s) and any optional agents such as crosslinking agents, therapeutic agents, and so forth, and (b) subsequently removing the solvent. The solvent that is ultimately selected will contain one or more solvent species, which are generally selected based on their ability to dissolve the polymer(s) that form the polymeric component, in addition to other factors, including drying rate, surface tension, etc. In certain embodiments, the solvent is selected based on its ability to dissolve or disperse the optional agents, if any. Solvent-based techniques include, but are not limited to, fiber forming techniques, solvent casting techniques, spin coating techniques, web coating techniques, spraying techniques, dipping techniques, techniques involving coating via mechanical suspension including air suspension, ink jet techniques, electrostatic techniques, and combinations of these processes.

In some embodiments of the invention, a polymer containing solution (where solvent-based processing is employed) or a polymer containing melt (where thermoplastic processing is employed) is applied to a substrate to form a polymeric component. For example, the substrate can correspond to all or a portion of an implantable or insertable medical device body to which a polymeric coating is applied, for example, by spraying, extrusion, and so forth. The substrate can also be, for example, a template, such as a mold, from which a polymeric component is removed after solidification. In other embodiments, for example, extrusion and co-extrusion techniques, polymeric components may be formed without the aid of a substrate. In a specific example, a medical device body or device body precursor (e.g., a tube that is formed into a stent) is extruded. In another example, a polymeric coating layer is co-extruded along with an underlying medical device body or device body precursor.

Various crosslinking techniques can be used to crosslink bioabsorbable polymeric device components in accordance with the invention. In general, sites for crosslinking of the polymer may be located along the polymer backbone, on groups pendant to the backbone and/or end-groups of the polymer chain. Several crosslinking techniques will now be described.

Crosslinking may be evidenced by a plateau modulus for the material at lower frequencies and higher temperatures.

For example, free radical crosslinking may be employed in certain embodiments in which the polymer is crosslinked optionally using one or more polyunsaturated agents and a source of free radicals, for example, exposure to radiation or chemical free radical sources such as peroxides.

A commonly employed polyunsaturated agent is triallyl isocyanurate (TAIC). Other polyunsaturated agents include those described in U.S. Pat. No. 4,900,792 to Chen et al. and include diallyl compounds, triallyl compounds, and dimethacrylate compounds, among others. Illustrative of the diallyl compounds are diallyl itaconate, and diallyl phthalate, among others. Illustrative of triallyl compounds (in addition to TAIC above) are triallyl trimellitate, triallyl trimethallyl trimellitate, triallyl cyanurate, and triallyl phosphate, among others. Illustrative of dimethacrylate compounds are ethylene dimethacrylate, polyethylene glycol dimethacrylate, and trimethylol propane trimethacrylate, among others.

Examples of radiation which can be used to generate free radicals include, for example, penetrating charged particles such as e-beam radiation, and electromagnetic radiation such as UV or X-ray radiation.

Examples of peroxides include those capable of free radical generation on thermal and/or radiation exposure such as those set forth in U.S. Pat. No. 4,900,792, including bis(t-alkylperoxy) alkanes, bis(t-alkylperoxy) benzenes, and bis(t-alkylperoxy) acetylenes. Illustrative of bis(t-alkylperoxy) alkanes are 2,5-bis(t-amylperoxy)-2,5-dimethylhexane, 2,5-bis(t-butylperoxy)-2,5-dimethylhexane, 3,6-bis(t-butylperoxy)-3,6-dimethyloctane, 2,7-bis(t-butylperoxy)-2,7-dimethyloctane and 8,11-bis(t-butylperoxy)-8,11-dimethyloctadecane, among others. Illustrative of the bis(t-alkylperoxy)benzenes are a,a'-bis(t-amylperoxy-isopropyl)-benzene, among others. Illustrative of bis(t-alkylperoxy) acetylenes are hexynes, octynes, and octadiyenes, for example, 2,7-dimethyl-2,7-di(t-butylperoxy)octadiyne-3,5, 3,6-Dimethyl-3,6(t-butylperoxy)octyne-4, and 2,5-dimethyl-2,5-di(t-butylperoxy)hexyne-3, among others.

In other embodiments, nucleophilic addition or substitution crosslinking may be employed in which the polymer is crosslinked using a polyfunctional nucleophile capable of reacting with the polymer backbone or suitable pendant group such as fluorinated alkenes, nitriles, carbonyls, alcohols and halogenated alkyls, to name a few. In addition, a coagent such as an acid acceptor and/or a phase transfer catalyst may also be employed, in certain instances.

Polyfunctional nucleophiles include those set forth in U.S. Pat. No. 4,882,390 to Kolb, for example, polyhydroxy compounds such as aromatic polyhydroxy compounds and aliphatic polyhydroxy compounds. Representative aromatic, polyhydroxy compounds include di-, tri-, and tetrahydroxy-benzenes, naphthalenes, and anthracenes, and bisphenols, specific examples of which include 4,4'-thiodiphenol, isopropylidene-bis(4-hydroxybenzene) (i.e. bisphenol A) and hexafluoroisopropylidene-bis(4-hydroxybenzene) (i.e. bisphenol AF), among others. Representative aliphatic polyhydroxy compounds include fluoroaliphatic diols, e.g. 1,1,6,6-tetrahydrooctafluorohexanediol, among others.

In other embodiments, crosslinking chemistries may be employed, which result in the formation of metallic salts to form an ionomeric crosslinked system.

In certain crosslinking processes, aliphatic polyesters such as poly(epsilon-caprolactone) (PCL), poly(butylene succinate) (PBS) or poly(lactide) (PLA) are radiation crosslinked in the presence of polyfunctional monomers such as triallyl-isocyanurate (TAIC) or trimethallylisosyanurate (TMAIC), among others. See S. Yoshii et al., IRaP 2002, 5th International Symposium on Ionizing Radiation and Polymers, Sep. 21-26, 2002, Hôtel Le Chantecler, Sainte-Adèle, Canada, P-060.

In yet another crosslinking process, PLA compounds composed of a furan-modified poly(lactide) and a maleimide linker are cross-linked by the Diels-Alder cyclo-addition between the furan and maleimide functions. M. Yamashiro et al., *Polymer Journal*, 40(7), 2008, 657-662.

As indicated above, in some embodiments, bioabsorbable device components such as those described elsewhere herein include one or more therapeutic agents. "Therapeutic agents," "drugs," "bioactive agents," "pharmaceuticals," "pharmaceutically active agents", and other related terms may be used interchangeably herein and include genetic therapeutic agents, non-genetic therapeutic agents, and cells. Therapeutic agents may be used singly or in combination. A wide range of therapeutic agent loadings can be used in conjunction with the devices of the present invention, with the pharmaceutically effective amount being readily determined by those of ordinary skill in the art and ultimately depending, for example, upon the condition to be treated, the nature of the therapeutic agent itself, the tissue into which the dosage form is introduced, and so forth.

Some specific beneficial agents include anti-thrombotic agents, anti-proliferative agents, anti-inflammatory agents, anti-migratory agents, agents affecting extracellular matrix production and organization, antineoplastic agents, anti-mitotic agents, anesthetic agents, anti-coagulants, vascular cell growth promoters, vascular cell growth inhibitors, cholesterol-lowering agents, vasodilating agents, and agents that interfere with endogenous vasoactive mechanisms.

Specific agents include taxanes such as paclitaxel, olimus family drugs such as sirolimus, everolimus, biolimus and tacrolimus, Epo D, dexamethasone, estradiol, halofuginone, cilostazole, geldanamycin, ABT-578 (Abbott Laboratories), trapidil, liprostin, Actinomcin D, Resten-NG, Ap-17, abciximab, clopidogrel, Ridogrel, beta-blockers, bARKct inhibitors, phospholamban inhibitors, and Serca 2 gene/protein, resiquimod, imiquimod (as well as other imidazoquinoline immune response modifiers), human apolioproteins (e.g., AI, AII, AIII, AIV, AV, etc.), vascular endothelial growth factors (e.g., VEGF-2), as well a derivatives of the forgoing, among many others.

Numerous additional therapeutic agents useful for the practice of the present invention may be selected from those described in paragraphs [0040] to [0046] of commonly assigned U.S. Patent Application Pub. No. US 2003/0236514 to Schwarz, the entire disclosure of which is hereby incorporated by reference.

EXAMPLE

Plastic pellets consisting of poly(L-lactic acid) having intrinsic viscosity of 1 dL/g (0.1% solution, $CHCl_3$, 25 C) are first pre-mixed with 0.1 weight per cent triallyl isocyanurate and subsequently extruded on a single screw extruder to form tubing having inner diameter of 3 mm and wall thickness of 0.2 mm. The inserted tubing is then subjected to an axially and circumferentially uniform electron beam dosage of <5 kGy, sufficient to increase the intrinsic viscosity of the tubing material to >10 dL/g. The extruded and irradiated tubing is then cut into approximately 24 mm length sections for subsequent stent pattern formation. The extruded and irradiated tubing is then subjected to localized mass loss using a femtosecond-pulse laser to generate the desired stent pattern. Subsequent to pattern formation, the stent is compressed (crimped) onto a 3.0 mm diameter balloon with an iris-style crimper.

Although various embodiments are specifically illustrated and described herein, it will be appreciated that modifications and variations of the present invention are covered by the above teachings and are within the purview of the appended claims without departing from the spirit and intended scope of the invention.

The invention claimed is:

1. A method of forming a medical device comprising a bioabsorbable expandable device component that comprises a first biodegradable polymer having a glass transition temperature (Tg) above body temperature, said method comprising:
    crosslinking said device component in a first configuration,
    contracting said device component to a second configuration while heating said device component to an elevated temperature above said Tg, and
    cooling said device component while in said second configuration,
    wherein said medical device is a stent and wherein said bioabsorbable expandable device component is a stent body, and
    wherein said stent body in said second configuration is disposed on a balloon.

2. The method of claim 1, wherein the stent body is a laser cut stent body.

3. The method of claim 1, wherein said second configuration has a diameter that ranges from 20% to 50% of the diameter of said first configuration.

4. The method of claim 1, wherein said stent is a coronary stent, wherein said first configuration is an expanded configuration having a diameter ranging from 2 to 5 mm, and wherein said second configuration is a collapsed configuration having a diameter ranging from 1 to 1.5 mm.

5. The method of claim 1, wherein said stent body is collapsed onto a balloon at said elevated temperature.

6. The method of claim 1, wherein said stent is a balloon expandable stent, wherein said first configuration is an expanded configuration having a diameter greater than or equal to the fully expanded balloon diameter, and wherein said second configuration is a collapsed configuration having a diameter equal to the collapsed balloon diameter.

7. The method of claim 1, wherein said first biodegradable polymer is selected from polyesters, polycarbonates, poly (ortho esters), polyanhydrides, polyphosphazines and tyrosine-based polymers.

8. The method of claim 1, wherein said first biodegradable polymer is a homopolymer or copolymer comprising a monomer selected from lactide, glycolide, caprolactone, and combinations thereof.

9. The method of claim 1, wherein said first biodegradable polymer is poly(l-lactide).

10. The method of claim 1, wherein a polyunsaturated agent is employed as a crosslinking agent.

11. The method of claim 1, wherein said polyunsaturated agent is triallyl isocyanurate.

12. The method of claim 1, wherein a polyfunctional nucleophile is employed as a crosslinking agent.

13. The method of claim 1, wherein said device component is crosslinked using radiation.

14. The method of claim 1, further comprising applying a layer that comprises a second biodegradable polymer and a therapeutic agent, wherein said first and second biodegradable polymers may be the same or different.

15. The method of claim 14, wherein said therapeutic agent is an antirestenotic agent.

* * * * *